US008663718B2

(12) United States Patent
Rauchdobler

(10) Patent No.: US 8,663,718 B2
(45) Date of Patent: Mar. 4, 2014

(54) CACTUS FRUIT EXTRACT

(75) Inventor: Julian Rauchdobler, Leonding (AT)

(73) Assignee: Kaahee Research and Development GmbH, Leonding (AT)

( * ) Notice: Subject to any disclaimer, the term of this patent is extended or adjusted under 35 U.S.C. 154(b) by 155 days.

(21) Appl. No.: 13/144,693

(22) PCT Filed: Jan. 14, 2010

(86) PCT No.: PCT/EP2010/050366
§ 371 (c)(1),
(2), (4) Date: Jul. 14, 2011

(87) PCT Pub. No.: WO2010/081839
PCT Pub. Date: Jul. 22, 2010

(65) Prior Publication Data
US 2011/0268718 A1    Nov. 3, 2011

(30) Foreign Application Priority Data
Jan. 15, 2009   (AT) .................................. A 56/2009

(51) Int. Cl.
*A61K 36/33* (2006.01)
(52) U.S. Cl.
USPC .......................................... 424/767; 424/777
(58) Field of Classification Search
None
See application file for complete search history.

(56) References Cited

U.S. PATENT DOCUMENTS

| 2002/0102317 | A1 | 8/2002 | Gutterrez et al. | |
| 2004/0241288 | A1* | 12/2004 | Lahav et al. | 426/93 |
| 2005/0042311 | A1* | 2/2005 | Lee et al. | 424/767 |
| 2007/0134355 | A1 | 6/2007 | Nöldner et al. | |
| 2009/0117211 | A1* | 5/2009 | Schneider et al. | 424/747 |
| 2010/0323045 | A1 | 12/2010 | Pischel et al. | |

FOREIGN PATENT DOCUMENTS

| KR | 2005/0078080 | 10/2005 |
| WO | 03/037324 | 5/2003 |
| WO | 2008/038849 | 4/2008 |
| WO | 2008/120206 | 10/2008 |

OTHER PUBLICATIONS

Pittler et al., BMJ, 2005, 331:1515-1518.
Wiese J et al., Archives of Internal Medicine, Amercian Medical Association, Chicago, IL, vol. 164, Jun. 28, 2004, pp. 1334-1340.
Austrian Patent App. No. A 56/2009, Search Report of the Austrian Patent Office, Jan. 15, 2009.
International Preliminary Report on Patentability, International Patent Application No. PCT/EP2010/050366, Jul. 19, 2011 (translation).
International Search Report, International Patent Application No. PCT/EP2010/050366, Jun. 30, 2010.
Written Opinion of the International Searching Authority, International Patent Application No. PCT/EP2010/050366, Jun. 30, 2010 (with translation).

* cited by examiner

*Primary Examiner* — Chris R Tate
(74) *Attorney, Agent, or Firm* — Loza & Loza, LLP; Mchael F. Fedrick

(57) ABSTRACT

A method for producing a cactus fruit extract for use in formulating a beverage which can be used in the treatment of veisalgia.

10 Claims, No Drawings

CACTUS FRUIT EXTRACT

CROSS-REFERENCE TO RELATED APPLICATIONS

This application is the U.S. national stage of International Patent Application No. PCT/EP2010/050366, filed on Jan. 14, 2010 and entitled CACTUS FRUIT EXTRACT, which claims the benefit of priority from Austrian Patent Application No. A 56/2009, filed Jan. 15, 2009. The disclosures of the foregoing applications are incorporated herein by reference in their entirety.

The invention relates to a method for producing a cactus fruit extract and its use for formulating a beverage.

*Opuntias* are a plant genus of the cactus plant family (Cactaceae), which comprises about 190 species. The use of some types of *Opuntias* as food has been known for several hundred years already. Extracts from plant parts of *Opuntia ficus indica* ("OFI") are used for treating a number of disease states. Thus, the plant extract is said to have a pharmacological effect for treating nervous disorders or metabolic disorders.

WO 03/037324 A1 describes an ethyl acetate extract of *Opuntia ficus indica* fruit, stem or dried fruit for prophylaxis and treatment of Alzheimer's disease, stroke, Parkinson's disease, cell and tissue damage caused by ischemia, or cardiovascular diseases, like e.g. also cardiac infarction. In that, the antioxidative effect of the *Opuntia ficus indica* extract is used for protection against neural damage to nerve cells.

WO 2008/038849 A1 describes a butanol extract or acid hydrolyzate of *Opuntia ficus indica*, which can be administered as a tablet, pill, capsule, powder, elixir, solution, syrup or aerosol and can be used in the form of a pharmaceutical composition for treating nervous diseases, like diseases of the cranial nerves, cerebrovascular diseases, cardiovascular diseases, stroke, concussion, Alzheimer's disease, Parkinson's disease or cardiac infarction.

WO 2005/041994 A1 or DE 10350194 A1, respectively, describes the use of plant parts of *Opuntias* and extracts produced therefrom for treating depressive moods and disorders or other affective disorders, which can be influenced by antidepressants, like e.g. anxiety and panic disorders, bipolar depressions, somatization disorders and premenstrual syndrome as well as preliminary stages of such diseases.

US 2002/0102317 A1 describes the production of biological substances from *Opuntia ficus indica* by extraction of the skin of the dried fruit with an organic solvent.

EP 2057994 A1 describes a method for producing an extract from prickly pears by extracting plant parts.

Wiese et al. (Arch Intern Med 2004: 164, 1334-1340) describes capsules containing an extract from the fruit skin of the *Opuntia ficus indica* fruit, which due to its anti-inflammatory effect are used for treating veisalgia. The effectiveness, however, could not be confirmed in the study of Pitter et al. (BMJ 2005: 331, 1515-1518).

Generally, in the literature, *Opuntia* flowers are preferably used for producing extracts with a pharmacological effect. Thus, according to WO 2008/120206 A1, a water-soluble alcoholic extract of the *Opuntia ficus indica* flower is administered in the form of a capsule with a daily dose of 0.003 to 1 g per person for inhibiting the alpha 1-adrenoreceptor.

Due to the water-insoluble active agents and the manufacture with organic solvents, like alcohol or butanol, known extracts of *Opuntia ficus indica* are commonly provided as dry preparations, like e.g. capsules or highly concentrated alcoholic solutions, like e.g. elixirs. This form of administration, however, is often rejected by patients, in particular for treating minor disease conditions, like veisalgia.

The symptoms of veisalgia are discomfort and impairment of the physical and mental ability of a human being as a consequence of slight alcohol intoxication. Colloquially, the term hangover is common, too. In that, the triggering amount of alcohol for the symptoms may vary greatly from subject to subject. The symptoms described may impair the ability from hours up to days. The symptoms of veisalgia include headaches, an upset stomach, dry mouth, nausea or vomiting, respectively, and general indisposition. Frequently, gastritis (irritation of the gastric mucosa) causes vomiting in connection with loss of appetite. The mental and physical abilities can be restricted (e.g. listlessness, dizziness, difficulties to concentrate, memory loss, slight shaking). Partially, depressive moods up to anxiety states occur.

The object of the present invention is to provide an alternative formulation of an extract from *Opuntia ficus indica*, which enables the administration of the extract as a food supplement or also as a stimulant in a simple manner, which can be taken for minor disease conditions, like for example veisalgia, or for prophylaxis of veisalgia.

This object is solved according to the invention by a new method for producing an aqueous formulation of a cactus fruit extract, comprising the following steps: a) providing *Opuntia ficus indica* fruit, b) gradually extracting the fruit by using an organic solvent in a process having 2 or more stages, wherein the solvent concentration is gradually changed, c) separating the solvent, and d) formulating the extract into an aqueous solution having an organic solvent content of less than vol %, and having an extract concentration of at least 2.5 wt %.

The undesired extracting agent is preferably removed by conversion into a glycolic extract.

Monovalent alcohol is preferably used as the solvent, like a C1-C4-alcohol, in particular ethanol or butanol, ethyl acetate or acetone. For extraction, common processes for plant extraction are used, wherein here the cactus fruit, preferably in a peeled form, but also the entire fruit with its skin or only the fruit skin, is taken as the starting material. The starting material may include only the fruit, preferably washed and chopped up, but also further plant material, like flowers, stem, leaves, leaf shoots or seeds. The fruit may be chopped up as fresh fruit or dried, and is gradually treated with the extracting agent. For example, the fruit is extracted with the solvent using a process having 2 or more stages, wherein the solvent concentration is gradually changed, e.g. is gradually reduced starting with a solvent/water mixture with a high concentration, like in the range of 70 vol % to 40 vol %, or is increased reversely. For fractioned extraction with extracting agents having various alcohol contents, in the first fraction, the liquid from the fruit may serve as part of the extracting agent. Then the alcohol/water mixture is respectively used for further extraction.

Gradually lowering the alcohol content, more hydrophilic ingredients are extracted, too, so that the spectrum of active agents gets substantially wider. In this manner, beside the most different betalains, polyphenols, but also nitrogen-containing compounds, like taurine and free amino acids, are additionally co-extracted. With this gradual extraction, it could be demonstrated, that although starting with a high alcohol content, e.g. with more than 50 vol %, e.g. more than 60 vol %, in particular about 70 vol %, a concentrated extract with defined active agents is produced, which still can be mixed clear or only slightly opalescent.

Various polysaccharides or hydrocolloids, e.g. pectin, but also lipophilic components, e.g. sterols or liposoluble vitamins, which are rather unsuitable for aqueous beverages and may delay the uptake of the desired active agents, are not co-extracted by the preferred alcohol extraction.

Preferably, a multi-stage extraction in the form of a primary maceration with about 70 vol % of ethanol and subsequent percolations with graded alcohol content up to about 45 vol % is undertaken in order to obtain the best yields with the most interesting spectrum of active agents.

In addition, with the first extraction step, maceration at an alcohol content of more than 60 vol %, e.g. at about 70 vol %, it is possible to perform sterilization without preserving agents, which is not possible with a lower alcohol content. This is of significance insofar as this extract can also be used in non-alcoholic and non-preserved beverages. Furthermore, undesired accompanying substances, like mucilage, could be removed.

As the next step, the extract obtained from the gradual alcoholic extraction may be mixed with glycerin, and the alcohol may be distilled off, for example, under vacuum. The extract is then advantageously filtered.

According to the method according to the invention, it is for example possible to produce concentrated glycolic extracts from fresh *Opuntia* fruits without ethanol content, which dissolve clearly in aqueous media.

An exhaustive extraction process can be advantageous to obtain the ingredients in a concentrated form.

Preferably, a drug or fresh fruit, respectively, extraction ratio of at least 1:1 is set, in particular a ratio of 2:1 to 5:1, preferably about 3:1. The extract preferably contains 10 to 20% of solids or 20-50% of dry matter (non-volatizable substances, at 100-105° C. according to Ph. Eur), respectively.

Following extraction, the organic solvent is separated to such extent that an aqueous solution results. An aqueous solution in terms of the invention is understood as a formulation, which is substantially free from the organic solvents used for extraction, in particular with a content of organic solvent of less than 5 vol %, preferably less than 3 vol %, less than 2 vol %, less than 1 vol %, most preferably less than 0.5 vol %. The ethanol content in the extract is preferably reduced to below 1%; in case of acetone or methanol, the content of the organic extracting agent components should not exceed 0.05 vol %. Normally, this formulation is provided as an alcohol-free beverage. Furthermore, the extract may also be used as an additive to alcoholic beverages and as a concentrate.

Surprisingly, it showed that the substantial ingredients of the extract, like betalains, e.g. betanin, phyllocactin, indigoxanthin, as well as polyphenols, but also organic acids, taurine, proline, glutamine and other free amino acids, are found in the aqueous formulation according to the invention, also with a low or no alcohol content. These cannot be obtained by extraction of the OFI fruit with water alone.

The solvent is preferably separated by phase separation or evaporation, respectively, in particular cases also by spray-drying. Following concentration of the extract, this is formulated depending on the purpose of use and made durable, if necessary.

A dry extract or freeze-dried extract, respectively, but also the dried formulation according to the invention may be stored over a longer period of time before uptake with water or with an aqueous preparation, respectively. The dry formulation is preferably also suitable as a trade product for later filling.

According to the invention, a suitable formulation is provided, which corresponds to the purpose of use of the beverage. Thus, for the prophylaxis of veisalgia, a highly concentrated elixir can be provided, for treating already occurred symptoms, however, a diluted beverage is provided in order to cover the increased need for water. Orally administrable pharmaceutical ready-to-use formulations, e.g. a solution, syrup, but also dry powder, granules or sherbet for uptake with water, are likewise possible.

An extract content of at least 2.5 wt % for uptake of a sufficient dose with a pharmacological effect is preferred. The preferably used concentration lies at least at 3 wt %, preferably at least at 5 wt %, more preferred at least at 7 wt %, 9 wt % or 10 wt % up to 20 wt %. For special formulations, a concentration of up to 30 wt % can be selected. Particularly preferred formulations have a concentration of 3.2 wt %, for a preferred daily dose of about 5-30 g, particularly preferred 3-10 g. Concentrates are also offered with a concentration of about 14-16 wt % in order to provide a preferred daily dose of up to 50 g. In that it has to be observed that the formulation contains the active agents in a dissolved form in order to avoid suspended particles, which result in deposition of the extract in the reservoir. It may, however, also be advantageous to provide a concentrated beverage, which is mixed with an alcoholic beverage in order to contain an alcoholic solution of the ingredients. The formulation according to the invention can also be provided as a diluted "near water" beverage, preferably as a clear solution.

Preferably an air-tight container made of glass, PET or metal, e.g. aluminum, is used as the reservoir.

Further ingredients of the recipe are preferably selected from the group of taurine, anthocyanins, Acai berry extract, guarana, green tea extract, caffeine, fructose, saccharose, ginger components, betanin, vitamins, vitamin B1 and/or B12, pantothenic acid, in particular calcium salt, niacin, folic acid, biotin, pyridoxine and vitamin C, minerals, like calcium or magnesium, selenium, zinc, gluconate, coenzyme Q10, L-carnithine, lipoic acid and carbon dioxide, as well as further ingredients, which in a formulation to be orally administered or in a beverage, respectively, or as a food supplement usually contribute to consistency, aroma or taste improvement, like citric acid, Ginkgo biloba extract or natural aromas, like e.g. prickly pear aroma. As carrier, maltodextrin is preferably used.

If possible, the addition of chemical preserving agents, like benzoates or sorbates, is avoided.

For example, the following compositions are suggested:

Prophylaxis: "Up front" beverage

| | | |
|---|---|---|
| Prickly pear extract | ≥10 g/100 ml | |
| Taurine (liver-detoxifying) | 200 mg/100 ml | Water-soluble, odor- and tasteless |
| Anthocyanins/Acai berry extract (colorant, antioxidative) | 100-200 mg/100 ml | Water-soluble, odor- and tasteless (slightly sour) |
| Vitamins niacin, pyridoxine, pantothenic acid | 15% RDA/100 ml | Water-soluble, odor- and tasteless |
| Mineral (calcium) | 15% RDA/100 ml | Water-soluble, odor- and tasteless |
| Coenzyme Q10 ("energy-yielding") | 10 mg/100 ml | Water-soluble, odor- and tasteless |

Therapy: "Morning after" beverage

| | | |
|---|---|---|
| Prickly pear extract | ≥10 g/100 ml | |
| Guarana or green tea extract (natural caffeine) | 15 mg of caffeine/100 ml | Water-soluble, odorless, slightly bitter, but can be masked well |

-continued

| Ingredient | Quantity/Unit | |
|---|---|---|
| Vitamins thiamin, vitamin C, Vitamin B12, biotin, folic acid | 50% RDA/100 ml | Water-soluble, odor- and tasteless |
| Mineral mixture zinc, selenium, magnesium | 50% RDA/100 ml | Water-soluble, odor- and tasteless |
| Dried ginger root (anti-nausea) | 100 mg/100 ml | |
| Lipoic acid (energy-yielding) | 20 mg/100 ml | Water-soluble, odor- and tasteless |

Universally usable product according to the "single-product strategy"

| Ingredient | Quantity/Unit | |
|---|---|---|
| Opuntia extract | >10 g/100 ml | |
| Guarana (natural caffeine) | 50-100 mg of caffeine | Water-soluble, slightly colored, slightly bitter |
| Citric acid | 0.5-1.0 g | Water-soluble, sour |
| Gingko biloba extract or natural aromas | 0.1-0.5 g | Water-soluble, slightly colored, neutral in taste |
| Taurine | 0.2 g | Water-soluble, uncolored, neutral in taste |
| Calcium (org. salt, gluconate) | 0.2 g | Water-soluble, uncolored, neutral in taste |
| Magnesium (org. salt, gluconate) | 0.18 g | Water-soluble, uncolored, neutral in taste |
| Pantothenic acid (Ca salt) | 1.8 mg | Water-soluble, uncolored, neutral in taste |
| Niacin | 5.4 mg | Water-soluble, uncolored, neutral in taste |
| Pyridoxine (HCl) | 0.6 mg | Water-soluble, uncolored, neutral in taste |
| Vitamin C | 36 mg | Water-soluble, uncolored, slightly sour |

The formulation is preferably provided as a durable sales product with a shelf-life of at least 6 months, preferably at least 12 months. Therefore, a process step for sterilizing or preserving, respectively, is suggested, which preferably comprises physical treatment. In particular thermal treatment or treatment with acid, respectively, like with a pH in the range between 3.5 and 5.0, preferably pH 4, is suggested. The preferred thermal treatment is short-term heating to temperatures of up to 80° C., like in a continuous process with a treatment at 72° C. for the duration of 1-2 minutes, or with lower temperatures for a longer period, at about 60° C.+/−2° C. for a duration of 30 minutes, preferably in a batch process.

Gentle treatment for preservation has to be preferred in any case in order to only insubstantially reduce the ingredients, like betalains, polyphenols or nitrogen-containing compounds, like taurines and free amino acids.

According to the invention, the formulation is provided for treating veisalgia, in particular for prophylaxis and therapy of veisalgia, its symptoms and disease conditions associated therewith. The preferred dose for prophylaxis is at least about 100 ml, preferably at least 200 ml of the beverage, up to about 10 hours before the consumption of alcohol, but also taken immediately prior to drinking alcohol or together with the alcoholic beverage, respectively. For therapy, preferably within 24 hours following the consumption of alcohol, within about 12 hours, a dose of at least 200 ml, preferably at least 300 ml, but also at least 400 ml or more of the beverage is intended. The maximum daily dose is estimated at about 2000 ml in order to avoid indisposition due to the ingredients.

The invention is further described with the following example.

EXAMPLE

Preparation of an OFI Extract

For producing the extract, whole, unpeeled, however, with the prickles removed, fresh *Opuntia* fruit was used. The skin comprises the majority of the pharmacologically valuable ingredients, like betalains. Prior to processing, the fruit is washed, dried and then chopped in a cutter.

As extraction process, fractioned percolation with gradual reduction of the alcohol portion is used. Since the *Opuntia* fruit has a liquid content of about 85%, in order to obtain a defined extract, first determination of the loss of drying has to be performed in order to calculate the amount of ethyl alcohol to be added. The extraction liquid for the first fraction is composed of the liquid portion of the fruit and the added alcohol. A sub-amount of the alcohol is added in order to avoid a fermentation process. Once the required additional amount of alcohol has been determined and calculated, the remaining amount of alcohol is added immediately and briefly stirred. For the first batch fraction, the amount of alcohol is determined at about 70 vol % (63 wt %). For the subsequent fractions, the extraction mixture is gradually reduced to 45 vol % of alcohol, wherein the alcohol is mixed with water in advance.

In order to concentrate the extract, the collected extract fractions are concentrated in a rotary evaporator under vacuum under addition of ascorbic acid, until the amount of extract corresponds to a fresh plant/extract ratio of about 3:1 and has a dry residue content of more than 20%. Depending on the purpose of use, this extract is taken up with a sub-amount of glycerin, ethanol, glucose syrup, etc. and passed on to chemical analysis.

The invention claimed is:

1. A method for producing an aqueous formulation of a cactus fruit extract, comprising the following steps:
    a) providing *Opuntia ficus indica* fruit,
    b) extracting the fruit with an extraction mixture comprising an organic solvent which is a C1-C4 alcohol, wherein a concentration of the solvent in the mixture of more than 50% by volume is provided, and wherein the solvent concentration in the mixture is then reduced to a lower concentration of up to 45% by volume,
    c) separating the solvent from the extraction mixture to form an extract, and
    d) formulating the extract into an aqueous solution having an organic solvent content of less than 5 vol %, and having an extract concentration of at least 2.5 wt %.

2. The method according to claim 1, characterized in that said extract is formulated into the aqueous solution at a concentration of 2.5-20 wt %.

3. The method according to claim 1, characterized in that said solvent is ethanol or butanol.

4. The method according to claim 1, characterized in that said aqueous solution obtained in step d) is made storage stable with a physical treatment.

5. The method according to claim 4, characterized in that said physical treatment is comprised of one or more processes selected from the group consisting of an acid treatment and pasteurization.

6. An aqueous formulation comprising cactus fruit extract obtained by the method according to claim 1.

7. The aqueous formulation according to claim 6, wherein the formulation comprises 5-20 wt % of the cactus fruit extract.

8. The aqueous formulation according to claim 6, wherein the formulation comprises at least 10 wt % of the cactus fruit extract.

9. The aqueous formulation according to claim 6, characterized in that it further comprises one or more ingredients selected from the group consisting of taurine, anthocyanins, Acai berry extract, guarana, green tea extract, caffeine, fructose, saccharose, ginger components, betanin, vitamins, vitamin B1, vitamin B12, pantothenic acid, niacin, folic acid, biotin, pyridoxine and vitamin C, minerals, calcium, magnesium, selenium, zinc, gluconate, coenzyme Q10, L-carnitine, lipoic acid, and carbon dioxide.

10. A method for treating veisalgia in a subject in need thereof comprising administering to the subject a therapeutically effective amount of the aqueous formulation according to claim 6.

\* \* \* \* \*